(12) United States Patent
Kim et al.

(10) Patent No.: US 6,534,201 B2
(45) Date of Patent: Mar. 18, 2003

(54) ORGANOMETALLIC LUMINESCENT MATERIALS AND ORGANIC ELECTROLUMINESCENT DEVICE CONTAINING SAME

(76) Inventors: Youngkyoo Kim, Singaegum LG Apt. 209-1701, #455, Gaegum-dong, Pusanjin-gu, Pusan (KR), 614-110; Jae-Gyoung Lee, Ggachimaeul 410-1004, #63-65, Gumi-dong, Bundang-gu, Seongnam-shi, Kyounggi-do (KR), 463-500

( * ) Notice: Subject to any disclaimer, the term of this patent is extended or adjusted under 35 U.S.C. 154(b) by 0 days.

(21) Appl. No.: 09/942,778

(22) Filed: Aug. 31, 2001

(65) Prior Publication Data

US 2002/0045064 A1 Apr. 18, 2002

Related U.S. Application Data

(62) Division of application No. 09/336,713, filed on Jun. 21, 1999, now abandoned.

(30) Foreign Application Priority Data

Jun. 23, 1998 (KR) ............................................. 98-23645

(51) Int. Cl.$^7$ ................................................ H05B 33/14
(52) U.S. Cl. ....................... 428/690; 428/704; 428/917; 313/504; 313/506; 252/301.16; 252/302.26; 257/40; 257/103
(58) Field of Search ................................ 428/690, 704, 428/917; 313/504, 506; 252/301.16, 302.26; 257/40, 103; 585/400; 546/134

(56) References Cited

U.S. PATENT DOCUMENTS 5,755,999 A * 5/1998 Shi et al. ................ 252/301.16
6,083,634 A * 7/2000 Shi .............................. 428/690

\* cited by examiner

*Primary Examiner*—Deborah Jones
*Assistant Examiner*—Ling Xu

(57) ABSTRACT

An organometallic luminescent material selected from the group consisting of the compounds of formulae (I) to (V) of the present invention can emit blue, green and red lights.

3 Claims, 5 Drawing Sheets

ORGANOMETALLIC LUMINESCENT MATERIALS AND ORGANIC ELECTROLUMINESCENT DEVICE CONTAINING SAME

This is a divisional application of prior application Ser. No. 09/336,713 filed Jun. 21, 1999 now abandoned.

FIELD OF THE INVENTION

The present invention is directed to novel organometallic luminescent materials, and, more particularly, to a novel organometallic luminescent material having the capability of emitting a wide range of colors including blue and green light, and high thermal stability, and an organic luminescent device containing same.

BACKGROUND OF THE INVENTION

Conventional organometallic luminescent compounds used in organic electroluminescent devices are mostly complexes of di- or trivalent metals such as zinc and aluminium.

For example, U.S. Pat. No. 5,456,988 describes 8-hydroxyquinoline complexes of zinc, aluminium and magnesium as organic luminescent materials; U.S. Pat. No. 5,837,390 discloses magnesium, zinc and cadmium complexes of 2-(o-hydroxyphenylbenzoxazole); Japanese Patent Laid-Open Publication No. 07-133483 reports luminescent complexes of 2-(o-hydroxyphenylbenzoxazole) with divalent metals such as magnesium and copper; and U.S. Pat. No. 5,529,853, and Japanese Patent Laid-Open Publication Nos. 06-322362, 08-143548 and 10-072580 disclose divalent or trivalent metal complexes of 10-hydroxybenzo[10] quinoline.

The above organometallic luminescent compounds containing a divalent or trivalent metal have relatively loosely bound ligands and an extended system of conjugation. As a result, they are relatively unstable and emit green or red light but not a blue light.

Therefore, there has existed a need to develop an organometallic luminescent material having improved stability and light emission characteristics such as the capability of emitting a blue light.

SUMMARY OF THE INVENTION

Accordingly, it is a primary object of the present invention to provide a novel organometallic luminescent material having the stability and desired emission characteristics, and an organic luminescent device containing same.

In accordance with the present invention, there is provided an organometallic luminescent material selected from the group consisting of the compounds of formulae (I) to (V).

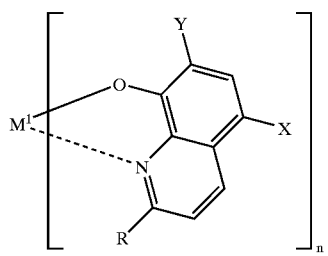
(I)

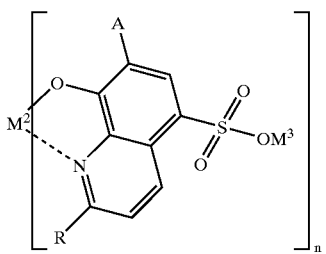
(II)

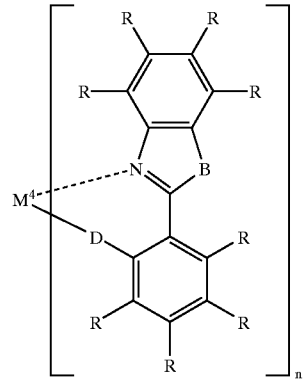
(III)

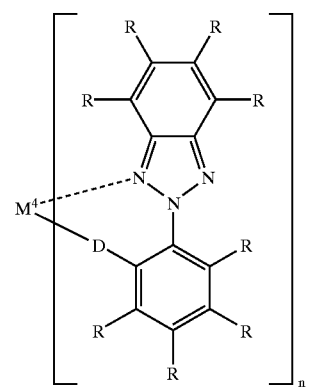
(IV)

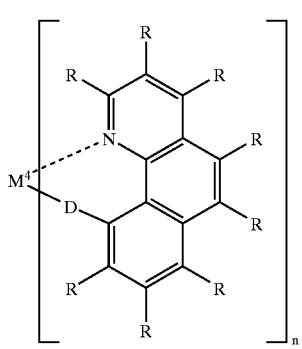
(V)

wherein, $M^1$ and $M^4$ are each independently a monovalent or tetravalent metal selected from the group consisting of Li, Na, K, Zr, Si, Ti, Sn, Cs, Fr, Rb, Hf, Pr, Pa, Ge, Pb, Tm and Md;

$M^2$ is a mono-, di-, tri- or tetravalent metal selected from the group consisting of Li, Na, K, Ca, Be, Ga, Zn, Cd, Al, Cs, Fr, Rb, Mg, Mn, Ti, Cu, Zr, Si, Hf, Pr, Pa, Ge, Sn, Pb, Tm and Md;

$M^3$ is selected from the group consisting of $Li^+$, $Na^+$, $K^+$, $Cs^+$, $Fr^+$, $Rb^+$, $Ca^{2+}$, $Be^{2+}$, $Ga^{3+}$, $Zn^{2+}$, $Al^{3+}$, $Mg^{2+}$, $Mn^{2+}$, $Ti^{2+}$ and $Cu^{2+}$;

R is a hydrogen or $C_{1-10}$ alkyl;

X and Y, which can be the same or different, are independently a hydrogen, Cl, F, I, Br or $SO_3H$;

A is a hydrogen, F, Cl, Br or I;

B is O, S, Se or Te;

D is O or S; and n is an integer ranging from 1 to 4.

DETAILED DESCRIPTION OF THE INVENTION

The organometallic luminescent materials of the present invention include 8-hydroxyquinoline-metal complexes of formula(I), 8-hydroxyquinoline-5-sulfonate-metal complexes of formula(II), benzoxazole-or benzthiazole-metal complexes of formula(III), benzotriazole-metal complexes of formula(IV), and benzoquinoline-metal complexes of formula(V).

Among the organometallic luminescent materials of the present invention, preferred are those listed in Table I.

TABLE I

| Formula | Compound No. | M* | $M_3$ | X | Y | A | B | D | n | R | $\gamma_{max}$ (nm) | color |
|---|---|---|---|---|---|---|---|---|---|---|---|---|
| (I) | 1 | Li | — | H | H | — | — | — | 1 | H | 495 | bluish green |
|  | 2 | Li | — | H | H | — | — | — | 1 | $CH_3$ | 490 | bluish green |
|  | 3 | Zr | — | H | H | — | — | — | 4 | H | 535 | light green |
|  | 4 | Zr | — | H | H | — | — | — | 4 | $CH_3$ | 532 | light green |
| (II) | 5 | Li | Li | — | — | H | — | — | 1 | H | 460 | blue |
|  | 6 | Li | Na | — | — | H | — | — | 1 | H | 462 | blue |
|  | 7 | Na | Li | — | — | H | — | — | 1 | H | 460 | blue |
|  | 8 | Na | Na | — | — | H | — | — | 1 | H | 463 | blue |
|  | 9 | Zn | Li | — | — | H | — | — | 2 | H | 461 | blue |
|  | 10 | Zn | Na | — | — | H | — | — | 2 | H | 464 | blue |
|  | 11 | Al | Li | — | — | H | — | — | 3 | H | 462 | blue |
|  | 12 | Al | Na | — | — | H | — | — | 3 | H | 465 | blue |
| (III) | 13 | Li | — | — | — | — | O | O | 1 | H | 450 | blue |
|  | 14 | Na | — | — | — | — | O | O | 1 | H | 455 | blue |
| (IV) | 15 | Li | — | — | — | — | — | O | 1 | H | 508 | green |
|  | 16 | Na | — | — | — | — | — | O | 1 | H | 512 | green |
| (V) | 17 | Li | — | — | — | — | — | O | 1 | H | 515 | green |
|  | 18 | Na | — | — | — | — | — | O | 1 | H | 650 | red |

Note:
M* is $M^1$, $M^2$ or $M^4$.

BRIEF DESCRIPTION OF THE DRAWINGS

The above and other objects and features of the present invention will become apparent from the following description thereof, when taken in conjunction with the accompanying drawings wherein.

Figure 1A:
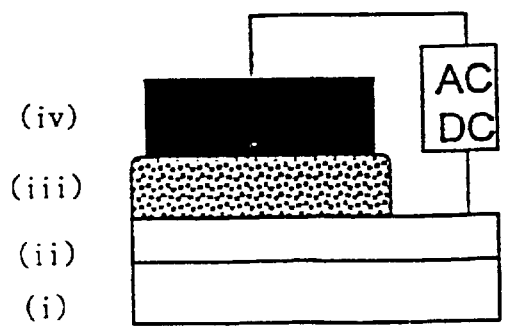
FIGS. 1a, 1b and 1c illustrate schematic diagrams of organic electroluminescent devices having an organic layer in the form of a single layer, a double layer or a multilayer, respectively.

The organometallic luminescent compound of the present invention may be prepared by reacting an organic compound that can serve as a ligand with an appropriate metal compound in a suitable solvent.

Exemplary solvents which can be used in the present invention include water, ethanol, methanol, propanol and the like.

Representative metal compounds that can be used to prepare the organometallic luminescent compounds of the present invention are LiOH, NaOH, KOH, NaCl, KCl, LiCl, $ZrCl_4$, $SnCl_4$, $TiCl_4$, $SiCl_4$, $BeCl_2$, $MgCl_2$, $AlCl_3$, $CaCl_2$, $ZnCl_2$ and the like.

Representative organic compounds which can be used as ligands in the present invention include 2-(2-hydroxyphenyl)benzoxazole, 8-hydroxyquinoline, 8-hydroxyquinoline-5-sulfonic acid, 2-(2-benzo-triazolyl)-p-cresol, 10-hydroxybenzoquinoline and the like.

The reaction of the organic and metal compounds to prepare the organometallic luminescent compound of the present invention may be carried out in a stoichiometric molar ratio which depends on n at a temperature ranging from 25 to 100° C. for 1 to 24 hours.

In the preparation of 8-hydroxyquinoline-5-sulfonate metal derivative of formula(II), 8-hydroxyquinoline-5-sulfonic acid and a suitable $M^2$ compound are reacted to give 8-hydroxyquinoline-5-sulfonate derivatives of formula (VI). Subsequently, the compound of formula(VI) is reacted with a compound of $M^3$ to obtain the 8-hydroxyquinoline-5-sulfonate derivative of formula (II).

Alternatively, the 8-hydroxyquinoline-5-sulfonate metal derivative of formula(II) may be prepared by a dry process. That is, a compound of formula (VI) and a compound of formula(VII) may be deposited separately on a substrate and an in-situ reaction thereof may be incurred, e.g., at 150 to 450° C. under a reduced pressure(about $10^{-6}$ torr). The metallation of the sulfonic acid group in accordance with the in-situ reaction of scheme 1 accompanies a blue shift in the emitted light. For example, the maximum wavelength of the emitting light of the compound of formula(VI) is 510 nm while that of the compound of formula(II) is 460 nm.

Scheme 1.

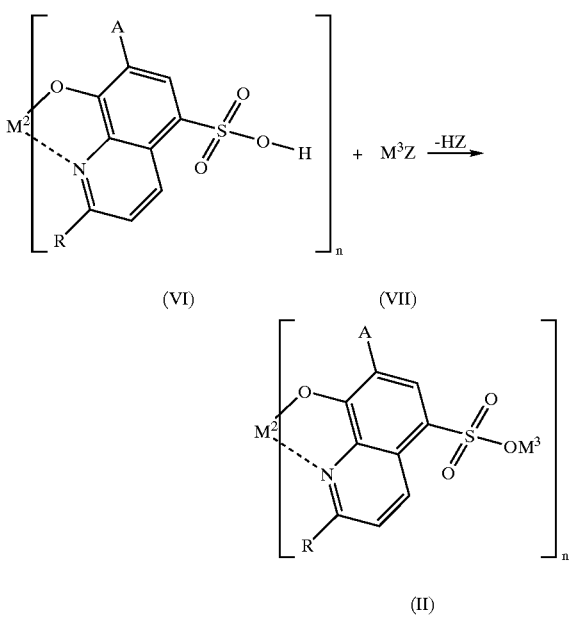

(VI)  (VII)

(II)

wherein, $M^2$, $M^3$ and n have the same meanings as defined above, and Z is a halogen atom or hydroxy group.

The organometallic complex of the present invention can be used as a luminescent doping material as well. For example, when it is doped in an amount of about 2% in a blue light emitting luminescent layer, the emitting light changes from blue to light blue or green. Accordingly, an efficient electroluminescent device capable of emitting a tuned color can be prepared.

The organic luminescent device of the present invention has a structure comprising an organic thin layer in the form of a single layer, or in the form of a double layer and multilayer containing a hole transporting layer and/or an electron transporting layer. In this case, the organometallic luminescent material of the present invention can be used alone, or in combination with a polymer or an inorganic material. Further, it may be doped in a polymer to give a fluorescent thin layer.

Figure 1B:
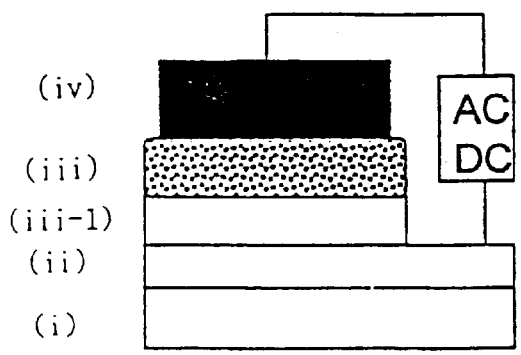
Figure 1C:
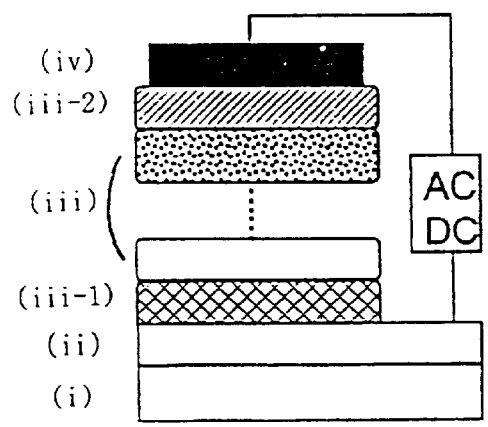

An example of the electroluminescent device of the present invention contains a single organic layer as shown in FIG. 1a. The device consists of (i) a glass substrate, (ii) a transparent ITO(indium tin oxides) anode electrode layer, (iii) an organic luminescent layer containing an organometallic luminescent material of the present invention, and (iv) a metal cathode electrode layer. Another example of the inventive device has an additional hole transporting layer (iii-1) as shown in FIG. 1b, or a multilayered structure shown in FIG. 1C wherein (iii-2) denotes an additional electron transporting layer. The electroluminescent device of the present invention may be operated with direct or alternative current, while the direct current is preferred.

The organic luminescent layer of the present invention may be formed by a conventional method including a wet process such as spin coating, and a dry process such as a vapor deposition, vacuum thermal deposition, sputtering and electron beam deposition method.

The novel organometallic luminescent compound of the present invention is capable of emitting blue, green or red light. The inventive complexes containing monovalent metals in particular are excellent blue light emitting luminescent materials which are stable even at a high temperature.

The present invention is further described and illustrated in Examples, which are, however, not intended to limit the scope of the present invention.

EXAMPLE 1

Preparation Compound 13

2-(2-hydroxyphenyl)benzoxazole and lithium oxide were added to 250 ml of ethanol in a molar ratio of 1:1 and the mixture was refluxed at 78° C. for 4 hours. The reaction mixture was filtered and the solvent and moisture were removed under a reduced pressure to give 2-(2-hydroxyphenyl)benzoxazole-lithium complex of formula (VIII) (compound 13).

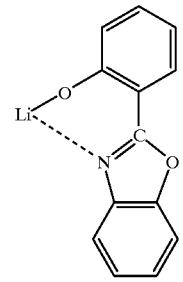

(VIII)

Figure 2:
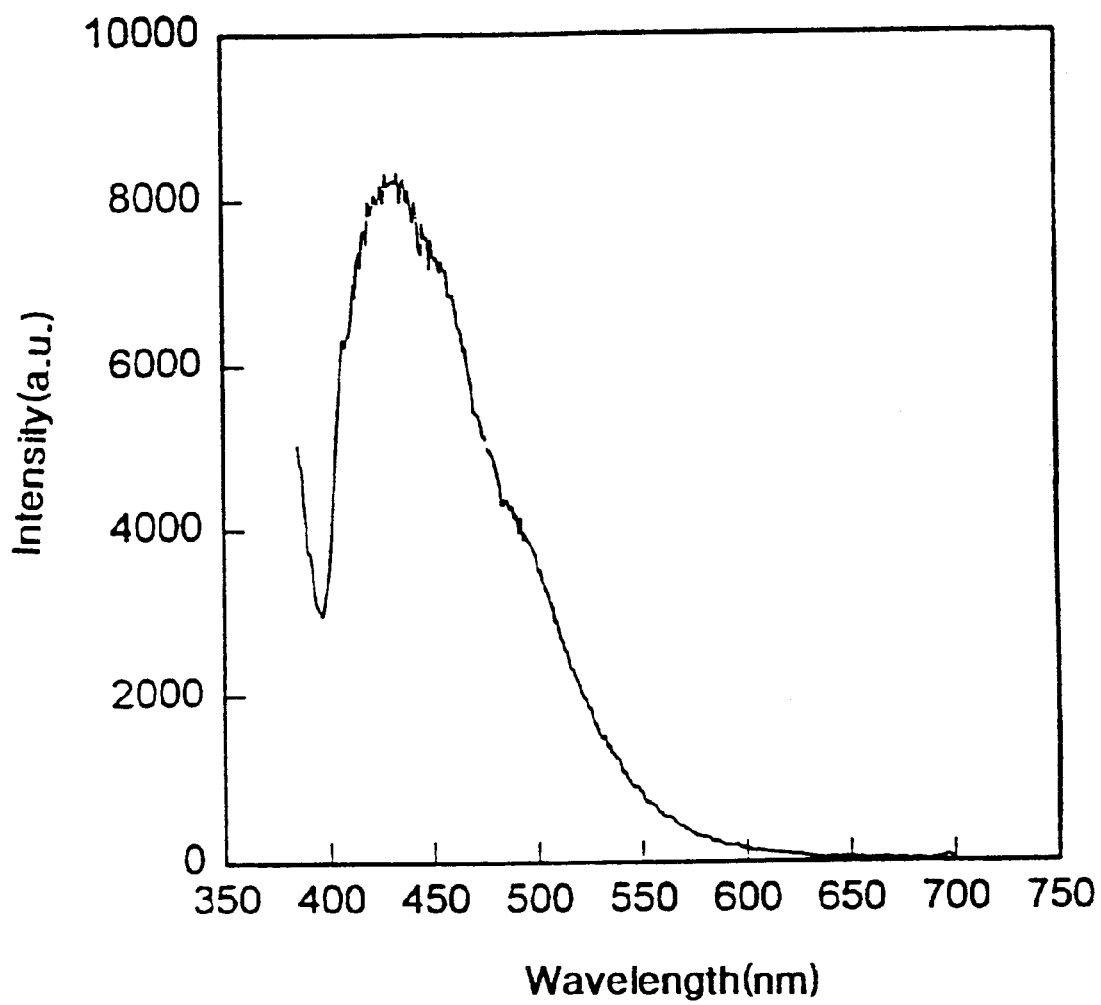
FIG. 2 shows the light emission spectrum of the organometallic luminescent material of Example 1 of the present invention.

FIG. 2 shows light emission spectrum of the complex thus obtained.

EXAMPLE 2

Indium-tin-oxide(ITO) was coated on a glass substrate to form a transparent anode layer. The coated substrate was subjected to photolithography and the patterned ITO glass was cleaned with a solution containing a non-phosphorous detergent, acetone and ethanol.

A mixture of polyetherimide of formula(IX) and triphenyldiamine of formula(X) in a weight ratio of 50:50 were dissolved in chloroform to a concentration of 0.5 wt %, and the resulting mixture was spin-coated on the ITO glass to form a hole transporting layer.

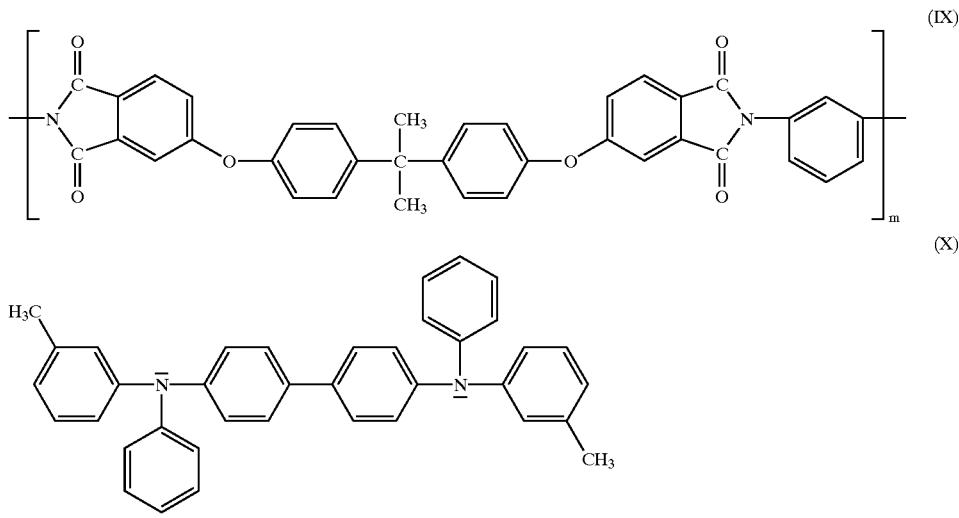

wherein m is an integer of two or higher.

2-(2-hydroxyphenyl)benzoxazole-lithium complex obtained in Example 1 was vapor deposited as a luminescent material on the hole transporting layer to a thickness of 20 nm to form an organic luminescent layer, and then, aluminium was vapor deposited to a thickness of 500nm to form a cathode layer. Subsequently, the device was packaged to obtain an electroluminescent device.

Figure 3:
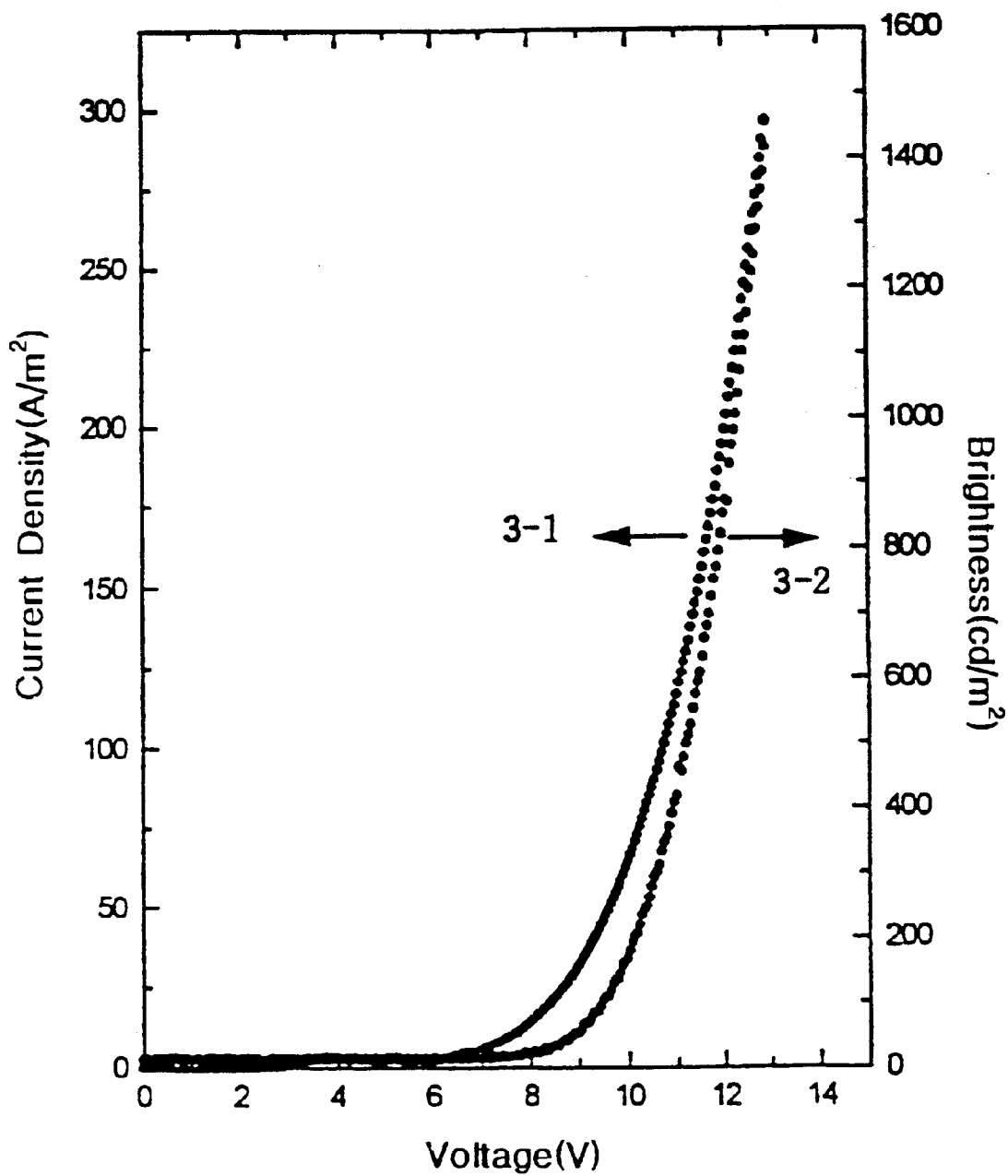
FIG. 3 demonstrates variations of the current density(A/$m^2$)(3-1) and brightness(cd/$m^2$)(3-2) of the electroluminescent device of Example 2 of the present invention as a function of applied voltage(V)
Figure 4A:
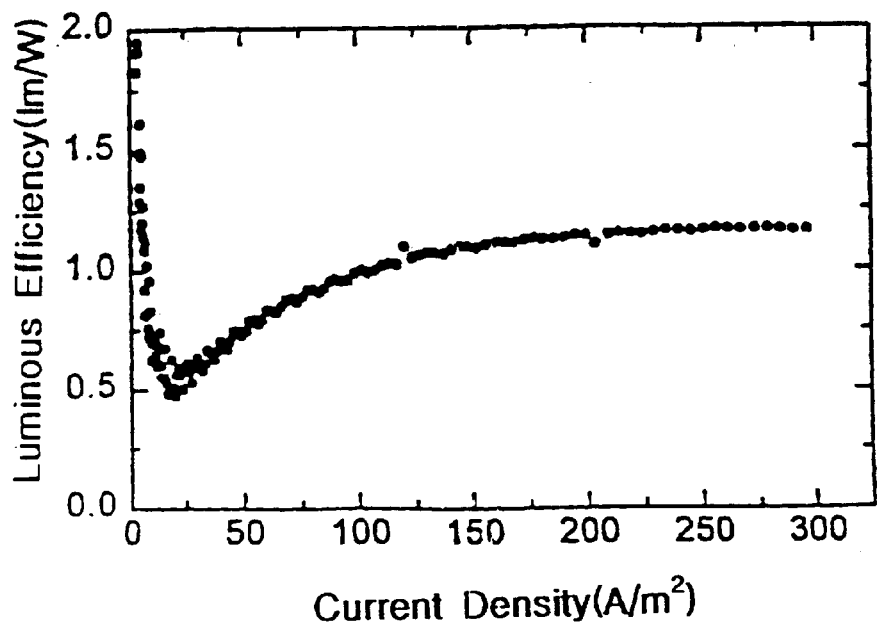
FIGS. 4a and 4b depict changes in the luminous efficiency(lm/W) of the electroluminescent device of Example 2 with current density(A/$m^2$) and brightness(cd/$m^2$), respectively.
Figure 4B:
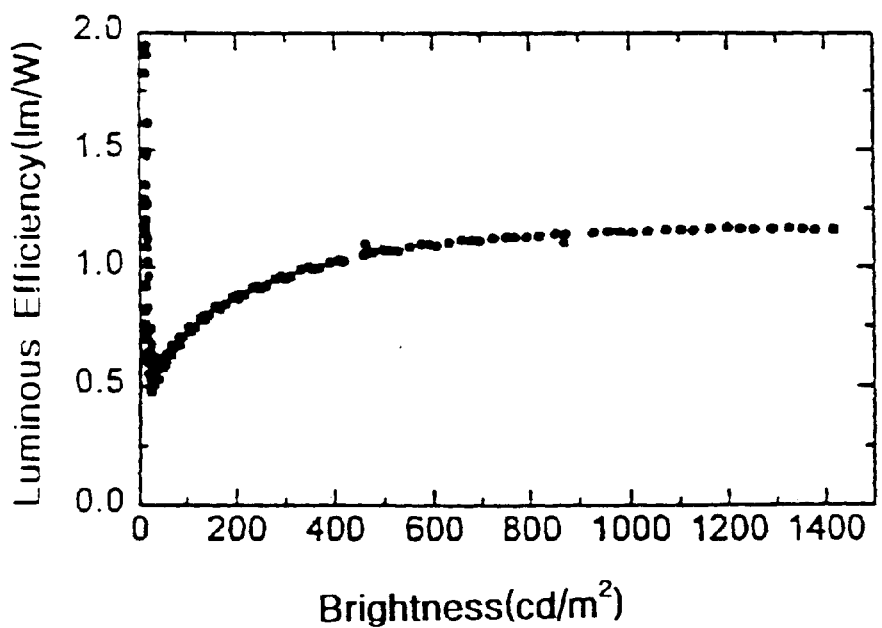
Figure 5:
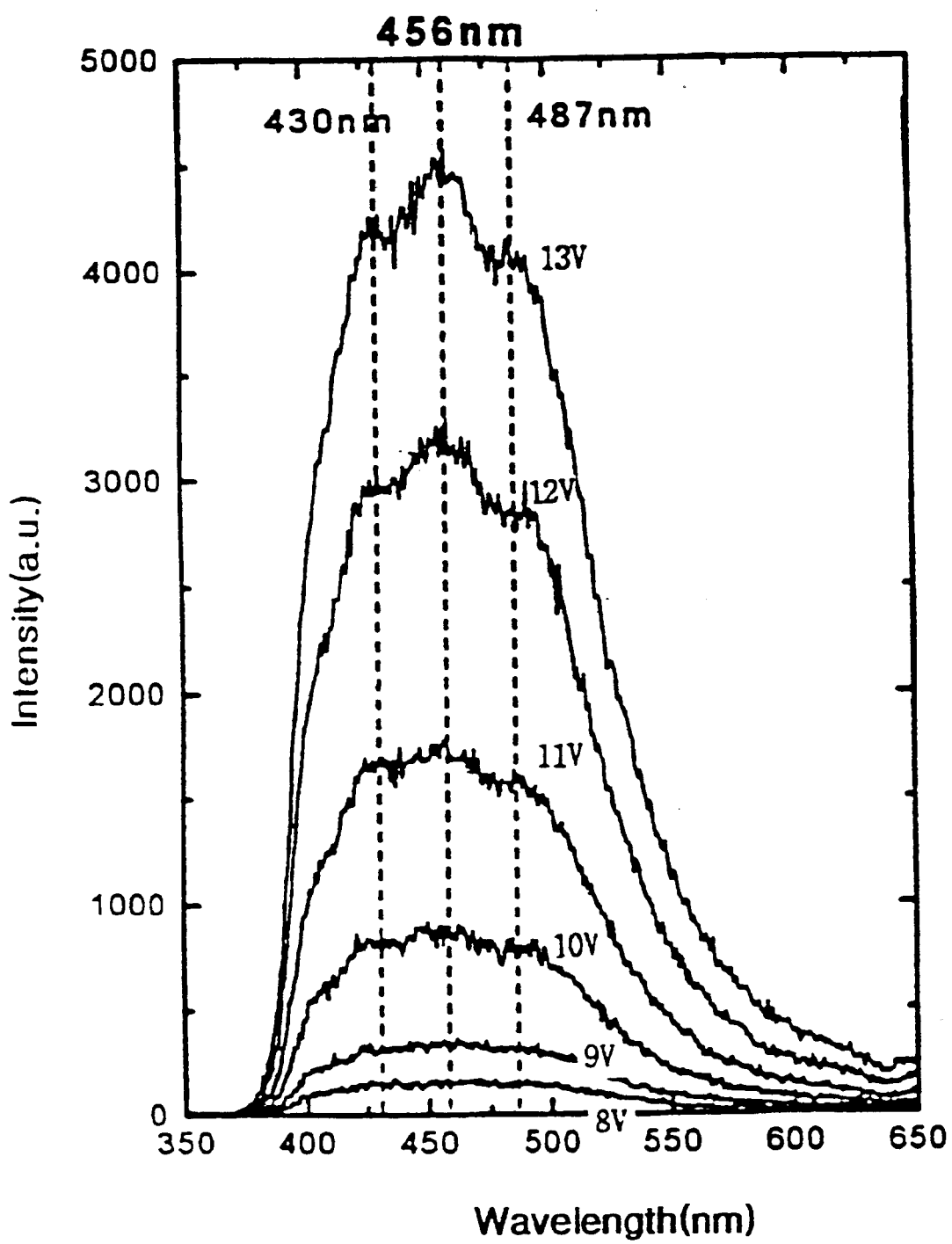
FIG. 5 exhibits the electroluminous spectra of the electroluminescent device of Example 2 of the present invention at various applied voltages(V).

The luminescence characteristics of the electroluminescent device are shown in FIGS. 3, 4 and 5.

FIG. 3 illustrates the variation of the current density(A/$m^2$) (3-1) and brightness(cd/$m^2$) of the electroluminescent device thus obtained as a function of the applied voltage(v). The current injection starts at about 6 V, turn on voltage is about 7 to 8 V, and the brightness is 500 cd/$m^2$ at 11 V.

FIGS. 4a and 4b depict the changes in the luminous efficiency(lm/W) of the above electroluminescent device with current density(A/$m^2$) and brightness(cd/$m^2$), respectively. The luminous efficiency is steady at 1.2 lm/W at a current density of 200 A/$m^2$ and beyond.

FIG. 5 exhibits electroluminous spectra of the above electroluminescent device at various applied voltages of 8, 9, 10, 11, 12 and 13 V. The main peak appears at 456 nm and shoulder peaks are observed at 430 and 487 nm. The emitted light is blue.

EXAMPLE 3

Preparation of Compounds 5 and 6

8-hydroxyquinoline-5-sulfonic acid and lithium hydroxide were added to 250 ml of ethanol in a molar ratio of 1:1 and the mixture was refluxed at 78° C. for 4 hours. The reaction mixture was filtered and dissolved in an excess amount of water. Subsequently, water was removed under a reduced pressure to obtain lithium complex of 8-hydroxyquinoline-(5-sulfonic acid)-(LiQSA).

LiQSA thus obtained and LiOH(or NaOH) were added to 100 ml of ethanol in a molar ratio of 1:1 and the mixture was reacted at a room temperature for 1 hour. Precipitates were separated from the reaction mixture and dried for 24 hours under a reduced pressure to obtain a lithium complex of lithium 8-hydroxyquinolinato-5-sulfonate (LiQSLi, Compound 5), or a lithium complex of sodium 8-hydroxyquinolinato-5-sulfonate (LiQSNa, Compound 6), respectively.

The maximum wavelength and emitted colors of the complexes thus obtained were measured and shown in Table I.

EXAMPLE 4

Preparation of Compounds 7 and 8

8-hydroxyquinoline-5-sulfonic acid and sodium hydroxide were added to 250 ml of ethanol in a molar ratio of 1:1 and the mixture was refluxed at 78° C. for 4 hours. The reaction mixture was filtered and dissolved in an excess amount of water. Subsequently, water was removed under a reduced pressure to obtain 8-hydroxyquinolin-(5-sulfonic acid) sodium complex (NaQSA).

NaQSA thus obtained and LiOH(or NaOH) were added to 100 ml of ethanol in a molar ratio of 1:1 and the mixture was reacted at a room temperature for 1 hour. Precipitates were separated from the reaction mixture and dried for 24 hours under a reduced pressure to obtain a sodium complex of lithium 8-hydroxyquinolinato-5-sulfonate (NaQSLi, Compound 7) or a sodium complex of sodium 8-hydroxyquinolinato-5-sulfonate (NaQSNa, Compound 8).

The maximum wavelengths and emitted colors of the complexes thus obtained were measured and shown in Table I.

EXAMPLE 5

Preparation of Compounds 9 and 10

8-hydroxyquinoline-5-sulfonic acid and zinc chloride (ZnCl$_2$) were added to 250 ml of ethanol in a molar ratio of 2:1 and the mixture was refluxed at 78° C. for 4 hours. The reaction mixture was filtered and dissolved in an excess amount of water. Subsequently, water and HCl were removed under a reduced pressure to give a zinc complex of bis(8-hydroxyquinolinato-5-sulfonic acid) (Zn(QSA)$_2$).

Zn(QSA)$_2$ thus obtained and LiOH(or NaOH) were added to 100 ml of ethanol in a molar ratio of 1:2 and the mixture was reacted at a room temperature for 1 hour. Precipitates were separated from the reaction mixture and dried for 24 hours under a reduced pressure to obtain a zinc complex of lithium bis(8-hydroxyquinolinato-(5-sulfonate) (Zn(QSLi)$_2$, Compound 9), or a zinc complex of sodium bis(8-hydroxyquinolin-5-sulfonate) (Zn(QSNa)$_2$, Compound 10).

The maximum wavelengths and emitted colors of the complexes thus obtained were measured and shown in Table I.

EXAMPLE 6

Preparation of Compounds 11 and 12

8-hydroxyquinoline-5-sulfonic acid and AlCl$_3$ were added to 250 ml of ethanol in a molar ratio of 3:1 and the mixture was refluxed at 78° C. for 4 hours. The reaction mixture was filtered and dissolved in an excess amount of water. Subsequently, water and HCl were removed under a reduced pressure to obtain aluminium tris(8-hydroxyquinolinato-5-sulfonic acid) (Al(QSA)$_3$).

Al(QSA)$_3$ thus obtained and LiOH (or NaOH) were added to 100 ml of ethanol in a molar ratio of 1:3 and the mixture was reacted at a room temperature for 1 hour. Precipitates were separated from the reaction mixture and dried for 24 hours under a reduced pressure to obtain an aluminium complex of lithium tris(8-hydroxyquinolin-(5-sulfonate)(Al(QSLi)$_3$, Compound 11), or an aluminium complex of sodium tris(8-hydroxyquinolin -5-sulfonate) complex (Zn (QSNa)$_3$).

The maximum wavelengths and emitted colors of the complexes thus obtained were measured and shown in Table I.

EXAMPLE 7

Preparation of Compound 14

2-(2-hydroxyphenyl)benzoxazole and NaOH were added to 250 ml of ethanol in a molar ratio of 1:1 and the mixture was refluxed at 78° C. for 4 hours. The reaction mixture was filtered and the solvent and moisture were removed under a reduced pressure to obtain 2-(2-hydroxyphenyl)-benzoxazole-sodium complex.

The maximum wavelength and emitted color of the complex thus obtained were measured and shown in Table I.

EXAMPLE 8

Preparation of Compounds 15 and 16

2-(2-hydroxybenzotriazole)-p-cresol and LiOH(or NaOH) were added to 250 ml of ethanol in a molar ratio of 1:1 and the mixture was refluxed at 78° C. for 4 hours. The reaction mixture was filtered and the solvent and moisture were removed under a reduced pressure to give 2-(2-hydroxybenzotriazole)-p-cresol-lithium complex (LiBTZC, Compound 15), or 2-(2-hydroxybenzotriazole)-p-cresol-sodium complex(NaBTZC, Compound 16).

The maximum wavelengths and emitted colors of the complexes thus obtained were measured and shown in Table I.

EXAMPLE 9

Preparation of Compounds 17 and 18

10-hydroxyquinoline and LiOH (or NaOH) were added to 250 ml of ethanol in a molar ratio of 1:1 and the mixture was refluxed at 78° C. for 4 hours. The reaction mixture was filtered and the solvent and moisture were removed under a reduced pressure to obtain 10-hydroxyquinoline-lithium complex(LiBQ, Compound 17), or 10-hydroxyquinoline-sodium complex(NaBQ, Compound 18).

The maximum wavelengths and emitted colors of the complexes thus obtained were measured and shown in Table I.

EXAMPLE 10

Preparation of Compound 3

8-hydroxyquinoline and ZrCl$_4$ were added to 250 ml of ethanol in a molar ratio of 4:1 and the mixture was refluxed at 78° C. for 4 hours. The reaction mixture was filtered and the solvent, HCl and moisture were removed under a reduced pressure to obtain tetra(8-hydroxyquiloninato)-zirconium complex (ZrQ$_4$, Compound 3).

The maximum wavelength and emitted color of the complex thus obtained were measured and shown in Table I.

As can be seen from the above result, the organometallic luminescent material of the present invention exhibits blue, green or red light emission. Therefore, an electroluminescent device containing the same is capable of exhibiting a full range of colors in the visible region with a high efficiency.

While the embodiments of the subject invention have been described and illustrated, it is obvious that various changes and modifications can be made therein without departing from the spirit of the present invention which should be limited only by the scope of the appended claims.

What is claimed is:

1. An electroluminescent device which comprises an organic luminescent layer containing the organometallic luminescent material comprising a compound of formula (II):

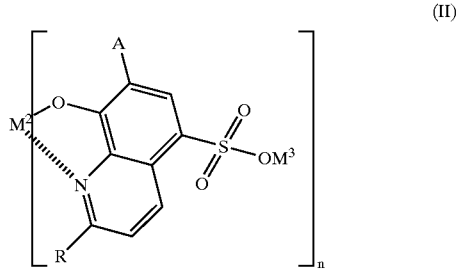

(II)

wherein,

M$^2$ is a mono-, di-, tri- or tetravalent metal selected from the group consisting of Li, Na, K, Ca, Be, Ga, Zn, Cd, Al, Cs, Fr, Rb, Mg, Mn, Ti, Cu, Zr, Si, Hf, Pr, Pa, Ge, Sn, Pb, Tm and Md;

M$^3$ is selected from the group consisting of Li$^+$, Na$^+$, K$^+$, Cs$^+$, Fr$^+$, Rb$^+$, Ca$^{2+}$, Be$^{2+}$, Ga$^{3+}$, Zn$^{2+}$, Al$^{3+}$, Mg$^{2+}$, Mn$^{2+}$, Ti$^{2+}$ and Cu$^{2+}$;

R is a hydrogen or C$_{1-10}$ alkyl;

A is a hydrogen, F, Cl, Br or I; and n is an integer ranging from 1 to 4.

2. The device of claim 1, wherein the organometallic luminescent material is present alone, or in combination with a polymer or an inorganic material, or in the form of a dopant in a polymer.

3. The device of claim 1, wherein the organic luminescent layer is formed by a spin coating, vapor deposition, vacuum thermal deposition, sputtering or electron beam deposition method.

* * * * *